US010517528B2

(12) United States Patent
Sinderby et al.

(10) Patent No.: US 10,517,528 B2
(45) Date of Patent: Dec. 31, 2019

(54) METHOD AND SYSTEM FOR VALIDATING INSPIRATORY MUSCLE ACTIVITY OF A PATIENT, AND MECHANICAL VENTILATION SYSTEM USING THE SAME

(71) Applicant: ST. MICHAEL'S HOSPITAL, Toronto (CA)

(72) Inventors: Christer Sinderby, Toronto (CA); Jennifer Beck, Toronto (CA); Norman Comtois, Scarborough (CA)

(73) Assignee: ST. MICHAEL'S HOSPITAL, Toronto, Ontario (CA)

( * ) Notice: Subject to any disclaimer, the term of this patent is extended or adjusted under 35 U.S.C. 154(b) by 475 days.

(21) Appl. No.: 15/105,613

(22) PCT Filed: Dec. 18, 2014

(86) PCT No.: PCT/CA2014/051234
§ 371 (c)(1),
(2) Date: Jun. 17, 2016

(87) PCT Pub. No.: WO2015/089668
PCT Pub. Date: Jun. 25, 2015

(65) Prior Publication Data
US 2016/0310069 A1    Oct. 27, 2016

Related U.S. Application Data

(60) Provisional application No. 61/917,499, filed on Dec. 18, 2013.

(51) Int. Cl.
*A61B 5/00*     (2006.01)
*A61B 5/0488*   (2006.01)
(Continued)

(52) U.S. Cl.
CPC .......... *A61B 5/4836* (2013.01); *A61B 5/0022* (2013.01); *A61B 5/0452* (2013.01);
(Continued)

(58) Field of Classification Search
CPC ....................................... A61B 5/08
See application file for complete search history.

(56) References Cited

U.S. PATENT DOCUMENTS 4,379,460 A * 4/1983 Judell .................. A61B 5/0809
                                                600/484
5,261,397 A * 11/1993 Grunstein .............. A61B 5/085
                                                128/204.18

(Continued)

FOREIGN PATENT DOCUMENTS

EP  1068975 A2  1/2001
EP  1896102 A1  3/2008
(Continued)

OTHER PUBLICATIONS

Duiverman et al., "Reproducibility and responsiveness of a noninvasive EMG technique of the respiratory muscles in COPD patients and in healthy subjects", J. Appl. Physiol. 96:1723-1729, 2004.

(Continued)

*Primary Examiner* — Tiffany Weston
(74) *Attorney, Agent, or Firm* — K&L Gates LLP

(57) ABSTRACT

The present disclosure relates to a method and a system for validating inspiratory muscle activity of a patient. Left and right electrical activity signals respectively representing activity of a left muscle and of a right muscle synchronized with an inspiratory effort of the patient are acquired from non-invasive sensors. A cardiac activity signal is extracted from the left and right electrical activity signals. A synchrony, a symmetry or a proportionality of the left and right electrical activity signals from which the cardiac activity (Continued)

signal is extracted is verified. A mechanical ventilation system incorporating the system for validating inspiratory muscle activity of the patient is also disclosed.

23 Claims, 9 Drawing Sheets

(51) Int. Cl.
*A61B 5/0452* (2006.01)
*A61M 16/00* (2006.01)
*A61B 5/113* (2006.01)
*A61B 5/08* (2006.01)

(52) U.S. Cl.
CPC ............ *A61B 5/0488* (2013.01); *A61B 5/113* (2013.01); *A61B 5/6819* (2013.01); *A61B 5/6822* (2013.01); *A61B 5/7207* (2013.01); *A61B 5/7246* (2013.01); *A61B 5/7278* (2013.01); *A61B 5/742* (2013.01); *A61M 16/0003* (2014.02); *A61B 5/08* (2013.01); *A61B 5/7214* (2013.01); *A61M 16/0051* (2013.01); *A61M 16/024* (2017.08); *A61M 2230/005* (2013.01); *A61M 2230/60* (2013.01)

(56) References Cited

U.S. PATENT DOCUMENTS

| | | | |
|---|---|---|---|
| 6,015,388 A | 1/2000 | Sackner et al. | |
| 6,059,010 A | 5/2000 | Yang | |
| 6,253,765 B1 | 7/2001 | Hognelid et al. | |
| 6,588,423 B1* | 7/2003 | Sinderby | A61B 5/04884 128/200.24 |
| 7,021,310 B1* | 4/2006 | Sinderby | A61B 5/0492 128/204.18 |
| 8,469,026 B2 | 6/2013 | Blomberg et al. | |
| 8,644,921 B2 | 2/2014 | Wilson | |
| 9,220,857 B2 | 12/2015 | Blomberg et al. | |
| 2005/0080463 A1* | 4/2005 | Stahmann | A61B 5/0488 607/62 |
| 2008/0121231 A1* | 5/2008 | Sinderby | A61B 5/037 128/204.21 |
| 2008/0308104 A1 | 12/2008 | Blomberg et al. | |
| 2009/0036790 A1 | 2/2009 | Landesberg et al. | |
| 2010/0252038 A1* | 10/2010 | Lagerborg | A61B 5/0488 128/204.23 |
| 2012/0132211 A1 | 5/2012 | Halperin et al. | |
| 2012/0253249 A1 | 10/2012 | Wilson | |
| 2013/0255686 A1 | 10/2013 | Blomberg et al. | |
| 2014/0296728 A1 | 10/2014 | Sinderby et al. | |
| 2015/0083135 A1* | 3/2015 | Cheng | A61M 16/0051 128/204.23 |

FOREIGN PATENT DOCUMENTS

| | | | |
|---|---|---|---|
| EP | 1068875 B1 | 9/2010 | |
| WO | WO 2005096924 A1 * | 10/2005 | ........... A61B 5/0488 |
| WO | 2012134505 A1 | 10/2012 | |
| WO | 2013071404 A1 | 5/2013 | |

OTHER PUBLICATIONS

Supplementary European Search Report for EP 14873101, date of completion: Jul. 31, 2017, 7 pgs.
International Search Report and Written Opinion from PCT/CA2014/051234 dated Mar. 20, 2015.
Emma Z. Hawkes et al. "Diaphragm and intercostal surface EMG and muscle performance after acute inspiratory muscle loading" Respiratory Physiology & Neurobiology, (2007), vol. 155, pp. 213-219.

* cited by examiner

METHOD AND SYSTEM FOR VALIDATING INSPIRATORY MUSCLE ACTIVITY OF A PATIENT, AND MECHANICAL VENTILATION SYSTEM USING THE SAME

CROSS REFERENCE TO RELATED APPLICATIONS

This is the national phase under 35 U.S.C. § 371 of International Application No. PCT/CA2014/051234, filed on Dec. 18, 2014, which claims priority to and the benefit of U.S. Patent Application No. 61/917,499, filed on Dec. 18, 2013, the entire disclosures of each of which are incorporated by reference herein.

TECHNICAL FIELD

The present disclosure relates to the field of mechanical ventilation systems. More specifically, the present disclosure relates to a method and a system for validating inspiratory muscle activity of a patient, and to a mechanical ventilation system that includes the system for validating inspiratory muscle activity of a patient.

BACKGROUND

A patient's inspiratory effort is difficult to determine from conventional measurements of airway pressure, flow, and volume waveforms displayed on a mechanical ventilator providing ventilatory assist to the patient. Thus, the accuracy by which ventilatory assist is delivered to the patient can be jeopardized by such measurements without the situation being noticed by the caregiver.

The main reason for this is that an airway pressure/flow sensor, airway impedance sensor, ultrasound sensor, ribcage movement sensor or other device that indicates the respiratory direction during unassisted breathing would be affected by mechanical ventilator's assist delivery.

Trans-esophageal measurements of diaphragm electrical activity (EAdi) provide sensitive and accurate determination of neural respiratory drive and are valid to determine patient-ventilator interaction. Techniques for obtaining and using such measurements are described in International Application Publication No. WO 2013/071404 to Sinderby et al., the disclosure of which is incorporated by reference herein in its entirety. However, these techniques use an esophageal catheter inserted in the patient's esophagus, the esophageal catheter comprising EAdi sensors mounted at the level where the esophagus passes through the diaphragm. Although esophageal catheters are frequently used to feed or medicate critically ill patients or to avoid aspiration in such patients, not all patients receive esophageal catheters.

Another method to measure electrical activity of inspiratory muscles uses surface electrodes placed on the neck and/or ribcage of the patient. However, due to the multilayered muscular architecture of the human body, electrical activity/surface electrode (EAse) signals may represent at once activity of inspiratory muscles as well as activity of intercostal muscles that may be activated to alter or maintain body posture of the patient. Surface electrodes will also detect electrical signals from the patient's heart. Conclusively, non-validated EAse signals do not provide sufficient and valid information related to inspiratory effort of a patient.

Therefore, there is a need for non-invasive methods and systems for obtaining validated information related to inspiratory effort of a patient when use of invasive sensors is avoided.

SUMMARY

According to the present disclosure, there is provided a method of validating inspiratory muscle activity of a patient. Left and right electrical activity signals, respectively representing activity of a left muscle and of a right muscle synchronized with an inspiratory effort of the patient, are acquired from non-invasive sensors. A cardiac activity signal is extracted from the left and right electrical activity signals. Verification is made of one or more of a synchrony, a symmetry or a proportionality of the left and right electrical activity signals from which the cardiac activity signal is extracted.

According to the present disclosure, there is also provided a system for validating inspiratory muscle activity of a patient. The validating system comprises non-invasive sensors that acquire left and right electrical activity signals that respectively represent activity of a left muscle and of a right muscle synchronized with an inspiratory effort of the patient. The validating system also comprises an extractor of a cardiac activity signal from the left and right electrical activity signals. The validating system further comprises a comparator that verifies one or more of a synchrony, a symmetry or a proportionality of the left and right electrical activity signals from which the cardiac activity signal is extracted.

The present disclosure further relates to a mechanical ventilation system including the above-defined validating system, a mechanical ventilator, a breathing tube providing ventilatory assist from the mechanical ventilator to a patient, and a controller operably connected to the validating system and controlling the mechanical ventilator based at least in part on a verification result from the first comparator.

The foregoing and other features will become more apparent upon reading of the following non-restrictive description of illustrative embodiments thereof, given by way of example only with reference to the accompanying drawings.

BRIEF DESCRIPTION OF THE DRAWINGS

Embodiments of the disclosure will be described by way of example only with reference to the accompanying drawings, in which.

Like numerals represent like features on the various figures of the drawings.

DETAILED DESCRIPTION

Figure 1:
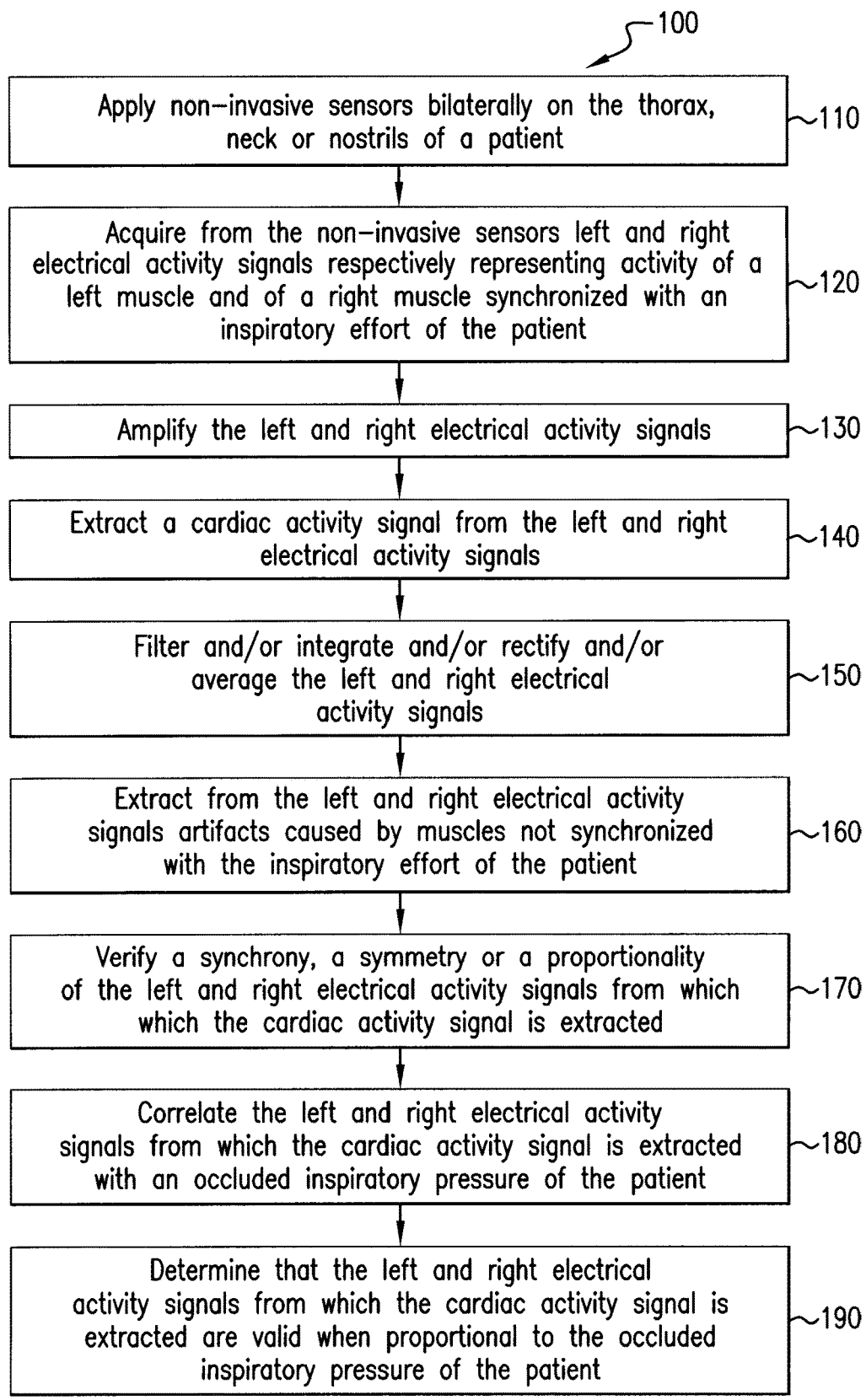
FIG. 1 is a flow chart showing operations of a method for validating inspiratory muscle activity of a patient according to an embodiment.

Various aspects of the present disclosure generally address one or more of the problems of obtaining validated information related to inspiratory effort of a patient when use of invasive sensors is avoided. The present disclosure introduce a method and a system for validating inspiratory muscle activity of a patient when electrical activity signals are obtained using non-invasive sensors. The present disclosure also introduces a mechanical ventilation system that incorporates the system for validating inspiratory muscle activity of a patient.

Generally stated, the disclosed technology validates measurements related to the inspiratory muscle activity of a patient, the measurements being obtained while avoiding the use of invasive sensors. Left and right electrical activity signals, respectively representing activity of a left muscle and of a right muscle synchronized with an inspiratory effort of the patient, are acquired from non-invasive sensors. A cardiac activity signal is extracted from the left and right electrical activity signals. A validation of the measurements is obtained, after the extraction of the cardiac activity signal, by verifying that the left and right electrical activity signals have a reasonable level of congruence. This verification may detect one or more of a synchrony, a symmetry or a proportionality of the left and right electrical activity signals.

The following terminology is used throughout the present disclosure:

Inspiratory muscle activity: detectable signal of an effort of a patient to breathe.

Non-invasive sensor: a measurement device, for example an electrode, that can be installed on a patient with minimal discomfort and with reduced impact on the patient's ability to move, speak, and the like.

Surface electrode: a type of non-invasive sensor that may be placed on the patient's body, generally on the skin.

Occluded inspiratory pressure: pressure measured during inspiration effort, while the airway of the patient is occluded.

Amplifier: an electronic device that increases the amplitude, intensity and/or power of a signal.

The following modules can be implemented as distinct hardware modules, including analog modules or digital modules. They may alternatively be implemented as software components in the form of computer executable instructions stored on a non-transient medium, the instructions being executable by a computer:

Extractor: removes a component from a complex signal.

Comparator: compares a signal with another signal or with a reference value.

Determiner: makes a logical decision based on a predetermined criterion.

Verifier: also makes a logical decision based on a predetermined criterion.

Filter, Integrator, Rectifier, and Averager: perform various processes on a signal in order to prepare the signal for analysis.

Some of the above modules may be combined in a same analog or digital hardware module. In some embodiments, some of these modules may be realized in the form of hardware devices while other modules may be realized as computer executable instructions. All possible analog and/or digital hardware and/or software combinations of those modules are within the scope of the present disclosure.

Referring now to the drawings, FIG. 1 is a flow chart showing operations of a method for validating inspiratory muscle activity of a patient according to an embodiment. The flow chart includes a sequence 100 comprising a plurality of operations that may be executed in variable order, some of the operations possibly being executed concurrently, some of the operations being optional.

Operation 110 comprises the application of non-invasive sensors bilaterally on the patient, for example on the thorax (such as in the region of the lower ribcage or para-sternally), neck or nostrils of the patient. In particular, the non-invasive sensors may be symmetrically placed on the patient's body on the left and right sides. In a non-limitative example, the non-invasive sensors may consist of two surface electrodes or may include a pair of electrode sets, each set including a plurality of electrodes.

At operation 120, left and right electrical activity signals respectively representing activity of a left muscle and of a right muscle synchronized with an inspiratory effort of the patient are acquired from the non-invasive sensors. Left and right muscles participating in the inspiratory effort of the patient may for example be located in the thorax (for example costal portion of the diaphragm, external intercostal, serratus anterior), neck (for example scalene, sternocleidomastoid) or nostrils (for example alae nasi) of the patient.

The left and right electrical activity signals are amplified at operation 130, before extracting a cardiac activity signal from the left and right electrical activity signals at operation 140. The left and right electrical activity signals may also be processed, at operation 150, by applying one or more of a filtering, integrating, rectifying, averaging processing to the left and right electrical activity signals.

At operation 160, artifacts caused by muscles not participating in the inspiratory effort of the patient are extracted from the left and right electrical activity signals. Generally, these artifacts may be non-symmetrical or may lack proportionality between left and right sides.

One or more of a synchrony, a symmetry or a proportionality of the left and right electrical activity signals from which the cardiac activity signal is extracted, for example a timing or amplitude synchrony, symmetry or proportionality of those signals, are verified at operation 170.

A correlation is made, at operation 180, of the left and right electrical activity signals from which the cardiac activity signal is extracted with an inspiratory pressure of the patient measured while the patient's airway is occluded.

It is determined at operation 190 that the left and right electrical activity signals from which the cardiac activity signal is extracted are valid when a sufficient level of synchrony, symmetry or proportionality is detected at operation 170 and/or when the left and right electrical activity signals are synchronized and proportional to the occluded inspiratory pressure of the patient as determined in correlation operation 180.

Optionally, some operations of the sequence 100 may be executed in a continuous fashion while some other operations may be executed at periodical intervals. For example, operation 170 to verify the synchrony, symmetry or proportionality of the left and right electrical activity signals from which the cardiac activity signal has been extracted may be made continuously, while operation 190 to determine that the left and right electrical activity signals from which the cardiac activity signal is extracted are synchronized and proportional to the occluded inspiratory pressure of the patient may be performed at periodical intervals.

Figure 2:
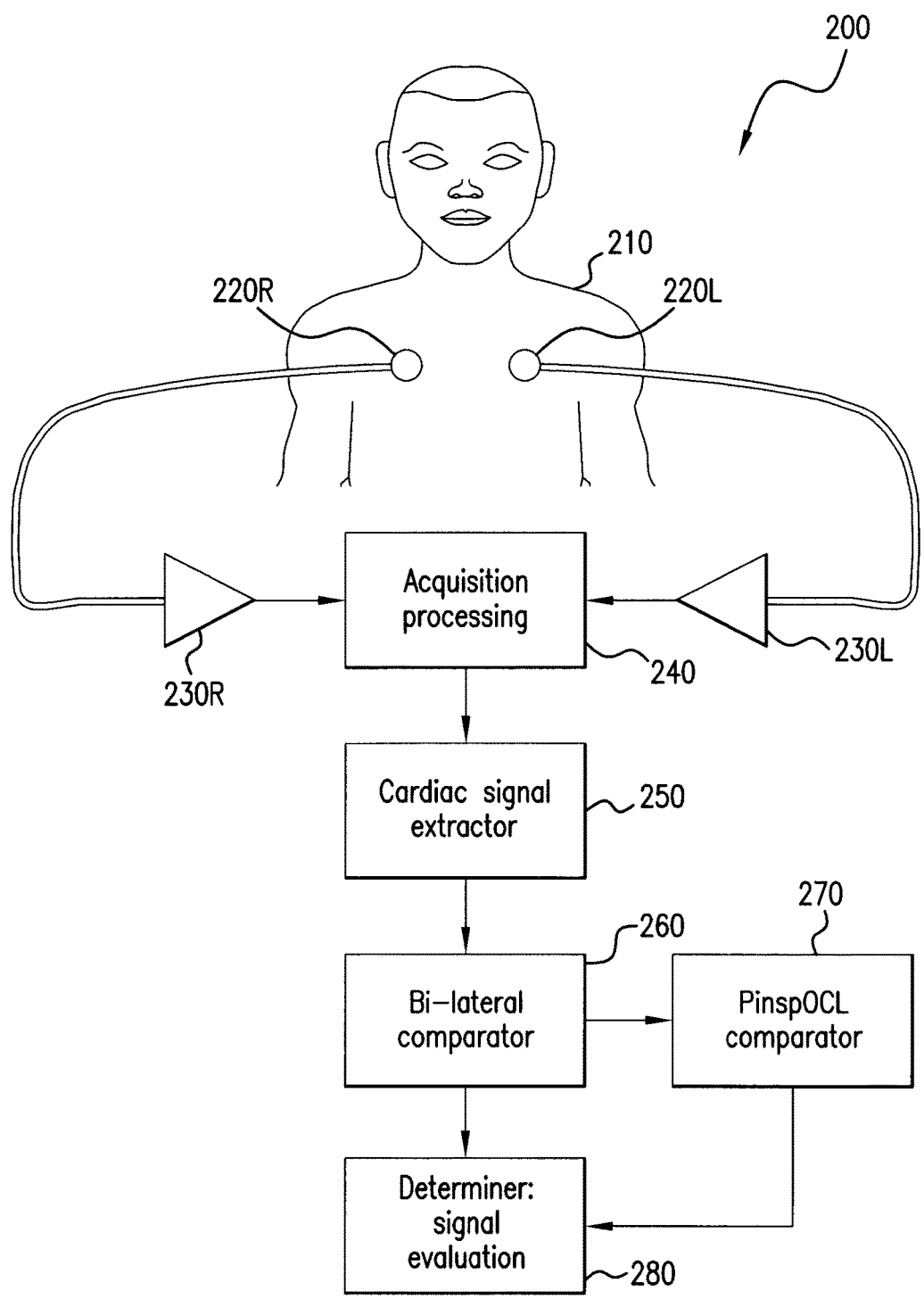
FIG. 2 is a block diagram of a system for validating inspiratory muscle activity of a patient according to an embodiment.

FIG. 2 is a block diagram of a system for validating inspiratory muscle activity of a patient according to an embodiment. The Figure shows a validating system 200 used to validate the inspiratory muscle activity of a patient 210. The validating system 200 includes two (2) non-invasive sensors 220L and 220R positioned on the body of the patient 210, and two (2) amplifiers 230L and 230R. The validating system 200 also includes several processing modules (or analog components having the same functions) that are described hereinbelow.

The non-invasive sensors 220L and 220R are configured to acquire left and right electrical activity signals respectively representing activity of a left muscle and of a right muscle synchronized with an inspiratory effort of the patient 210. The non-invasive sensors 220L and 220R are surface electrodes and may include a pair of electrode sets, each set including a plurality of electrodes. The non-invasive sensors 220L and 220R are configured for bilateral application on the body of the patient 210, for example on the left and right side of the thorax (such as in the region of the lower ribcage or para-sternally), neck or nostrils of the patient as described herein above. The bilateral application may for example involve a symmetrical application of the non-invasive sensors 220L and 220R on the patient's body. As indicated in the foregoing description, examples of left and right muscles in the thorax are the costal portions of the diaphragm, the external intercostals, and the serratus anterior muscles, examples of left and right muscles in the neck are the scalenes, and the sternocleidomastoids, and examples of left and right muscles in the nostrils are the alae nasi muscles of the patient.

Being optionally amplified by the amplifiers 230L and 230R, the left and right activity signals are provided to an acquisition processing module 240. The acquisition processing module 240 forwards the left and right activity signals to a cardiac signal extractor 250 that removes a cardiac activity signal from the left and right electrical activity signals. As well known to those of ordinary skill in the art, to remove the cardiac activity signal, the left and right electrical activity signals may be processed through an appropriately designed filter (not shown). The cardiac signal extractor 250 may also be designed to provide an indication, for example to an operator or to a caregiver, that a cardiac activity signal has not been properly detected in the left and right electrical activity signals. In this respect, the cardiac activity signal may be detected by sensing the high amplitude peak of the QRS complex.

Resulting left and right electrical activity signals from which the cardiac activity signal has been extracted are fed to a bi-lateral comparator 260. The bi-lateral comparator 260 verifies one or more of a synchrony, a symmetry or a proportionality, for example a timing or amplitude synchrony, symmetry or proportionality, of the left and right electrical activity signals from which the cardiac activity signal has been extracted. The comparator 260 may provide an indication to the operator or to the caregiver that the left and right electrical activity signals are not usable when symmetry, proportionality, or synchrony of the signals is lacking or is lower than a given level.

The result of the comparison made by the bi-lateral comparator 260 may be provided directly to a determiner 280 in order to validate the synchronized, symmetric or proportional left and right electrical activity signals. Alternatively or in addition, the result of the comparison made by the bi-lateral comparator 260 may be provided to a PinspOCCL (airway pressure during an occluded inspiration) comparator 270 that evaluates whether the synchronized, symmetric or proportional left and right electrical activity signals are synchronized and proportional to the inspiratory pressure of the patient measured while the patient's airway is occluded. The determiner 280 may use the result obtained from the PinspOCCL comparator 270 to further or better evaluate and validate the left and right electrical activity signals. Operation of the comparator 260 and determiner 280 will be further described in the following description.

In some embodiments, the validating system 200 may include one or more of a filter, an integrator, a rectifier and an averager of the left and right electrical activity signals. In the same or other embodiments, the validating system 200 may further include an extractor operative to remove from the left and right electrical activity signals non-symmetric artifacts caused by muscles not participating in the inspiratory effort of the patient. For example, without limitation, these elements may be made part of the acquisition processing module 240.

The non-symmetric artifacts may be removed from the left and right electrical activity signals through appropriate filtering or other electrical signal processing, depending on the nature of the artifact; such filtering or other processing is believed to be within the knowledge of those of ordinary skill in the art.

One or more of the acquisition processing module 240, the cardiac signal extractor 250, the bi-lateral comparator 260, the PinspOCCL comparator 270 and the determiner 280 may be integrated within a computer or within a plurality of interconnected computers.

In an embodiment, some of the modules of the validating system 200 may be integrated within a purpose-built device while some other modules of the validating system 200 may be integrated within a mobile terminal, for example a laptop computer, an intelligent mobile phone, a tablet computer, and the like. As a non-limitative example, the non-invasive sensors 220L and 220R may be connected to a device (not specifically shown) including the acquisition processing module 240 and a communication port (not shown) providing a connection via cable or via Bluetooth™ to a mobile terminal (not specifically shown) that includes the cardiac signal extractor 250, the bi-lateral comparator 260, the determiner 280 and, optionally, the PinspOCCL comparator 270. The modules implemented in the mobile terminal may be made available to the caregiver as a downloadable application. The mobile terminal can store data related to the validation of the respiratory signals for later processing, or transmit the data to a remote location via a cable, WiFi or cellular connection. This non-limitative example may be particularly useful in ambulatory applications in which the patient receives ventilatory assist at home or in an ambulance.

Figure 3:
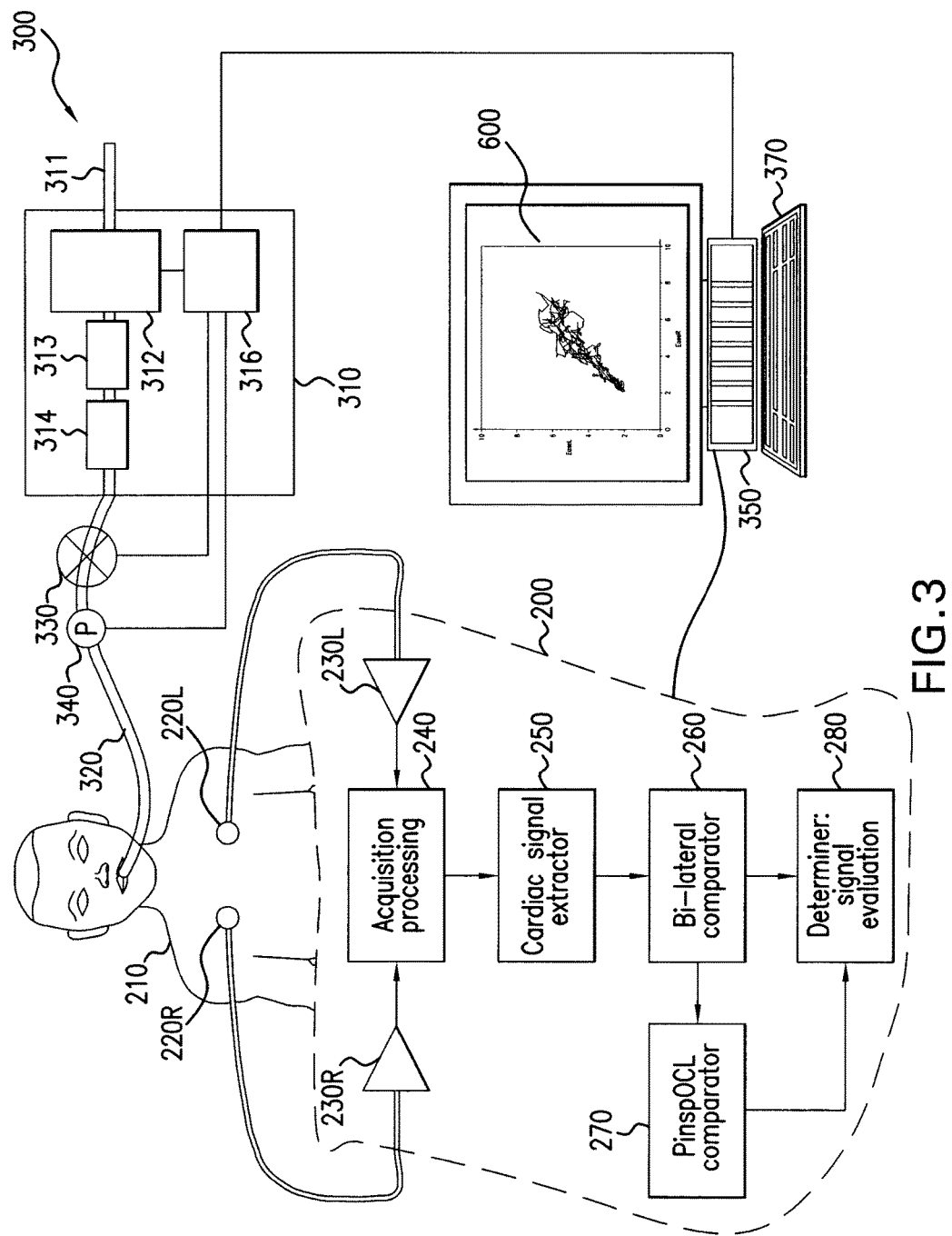
FIG. 3 is a block diagram of a mechanical ventilation system including the system for validating inspiratory muscle activity of a patient of FIG. 2.

FIG. 3 is a block diagram of a mechanical ventilation system including the system for validating inspiratory muscle activity of a patient of FIG. 2. A mechanical ventilation system 300 includes the various elements of the validating system 200 as well as a mechanical ventilator 310 providing ventilatory assist to an airway of the patient 210 via a breathing tube 320. In a non-limitative example, the mechanical ventilator 310 includes a gas connection 311 coupled to a gas source (not shown) and providing gas, such as air, oxygen, or any suitable breathing gas to a pneumatic unit 312 that may comprise inspiratory and expiratory valves (not specifically shown) and like devices for controlling a pressure and flow of a breathing gas. The breathing gas is output from the pneumatic unit 312 via the breathing tube 320 on which a pressure meter 313 and a flow meter 314 are mounted. The pneumatic unit 312 is controlled by an internal control unit 316. A more detailed, non-limitative example of a mechanical ventilator is described in European Patent Number 1 896 102 B1, the disclosure of which is incorporated by reference herein.

The breathing tube 320 may be attached to an endotracheal tube (not shown) insertable in the trachea of the patient 210, or may be attached to a mask (not shown) that can be placed on the face of the patient 210. An inspiratory valve 330 and an airway pressure meter 340 are mounted on the breathing tube 320. The inspiratory valve 330 is controllable by the control unit 316 of the mechanical ventilator 310 to cause an occlusion of the patient's inspiratory airway, allowing the control unit 316 to obtain from the airway pressure meter 340 a measurement of an occluded inspiratory pressure of the patient. The mechanical ventilation system 300 also includes a computer 350 that acts as a controller of the mechanical ventilator 310. The computer 350 may be an external component or may alternatively be integrated within the mechanical ventilator 310 as a part of the control unit 316. Regardless, the computer 350 provides an interface for feedback and control between the validating system 200 and the mechanical ventilator 310. The computer 350 further connects the validating system 200, via the control unit 316 of the mechanical ventilator 310, to the inspiratory valve 330 and to the airway pressure meter 340. The computer 350 is connected to a monitor 360 that allows display of various measurements and analysis results obtained by the validating system 200. The computer 350 may communicate with any one of the modules of the validating system 200.

Though the mechanical ventilation system 300 as illustrated provides ventilatory assist to the patient 210 via the breathing tube 320, the present disclosure encompasses any other type of mechanical ventilation systems. Any ventilation system capable of being controlled by an external computer or by an electromyogram (EMG) signal may be operated in combination with the validating system 200. Non-EMG examples of ventilation systems that may also be made part of the mechanical ventilation system are described in U.S. Pat. No. 6,253,765 B1 and in European Patent Number 1 068 875 B1.

In an embodiment, the interface between the mechanical ventilator 310 and the validating system 200 provided by the computer 350, supplies to the validating system 200 the measurement of the occluded inspiratory pressure of the patient obtained by the airway pressure meter 340. This interface may optionally enable adjustments of the mechanical ventilator 310 as a function of the validated inspiratory muscle activity of the patient 210, optionally under the control of a caregiver authorizing the adjustments using an operator interface 370, such as a keyboard, connected to the computer 350. In the same or other embodiment, the interface to the mechanical ventilator 310 provided by the computer 350 allows actuating the inspiratory valve 330 for reading the occluded inspiratory pressure of the patient at the airway pressure meter 340, the inspiratory valve 330 and the airway pressure meter 340 cooperating at that time with the PinspOCCL comparator 270. In a variant, the computer 350 and the monitor 360 may also alert the caregiver when the cardiac signal extractor 250 indicates that a cardiac activity signal is not properly detected in the left and right electrical activity signals. The computer 350 and the monitor 360 may further alert the caregiver that the left and right electrical activity signals are not usable because of an improper synchrony, symmetry or proportionality between the signals, when an indication to that effect is received at the computer 350 from determiner 280.

The validated inspiratory muscle activity of the patient obtained by the disclosed systems and method are usable for numerical or statistical analysis of an interaction between the patient and a ventilator, for analysis of a respiratory drive of the patient, for spectral analysis of respiratory muscle fatigue of the patient.

It should be understood that ultimate, final determination of the validity of the inspiratory muscle activity of the patient is a professional skill of the caregiver having expertise in the application of ventilatory assist to a patient. The technology disclosed herein provides valuable information to the caregiver about the synchrony, symmetry or proportionality of the electrical activity signals, facilitating such final professional determination.

Other uses of the electrical activity signals obtained and processed using the system and method for validating inspiratory muscle activity of a patient are within the scope of the present disclosure.

The following paragraphs provide theoretical and experimental support for the above described system and method. These paragraphs are mainly expressed in terms of signals obtained using surface electrodes, mentioning for example 'EAse' signals, i.e. electrical activity signals obtained using surface electrodes. However, it should be kept in mind that the teachings of the present disclosure related to left and right electrical activity signals measured through surface electrodes are also applicable to left and right electrical activity signals obtained through other types of suitable non-invasive sensors. In other words, the present disclosure is not limited to surface sensors but contemplates the use of other types of non-invasive sensors capable of providing the above described left and right electrical activity signals. As a result, mentions of 'EAse' signals and mentions of signals related to 'EAse' are made for the purpose of simplification only, not for the purpose of limiting the scope of the present disclosure.

In the present disclosure, a method and a system using EAse signals have been presented, in which multiple surface electrodes or electrode sets are placed on the patient's skin in areas exposed to the electrical activity of inspiratory muscles. The electrodes or electrode sets may be positioned bilaterally and symmetrically to measure bilateral activity of the inspiratory muscles, as described herein above.

Measurement of electrical activity using surface electrodes (EAse) is obtained from at least two electrodes (or two electrode sets) placed on the skin surface. However, other additional electrodes such as fine wires or needle electrodes applied to the patient's body can be used to provide a so called differential amplification of the signals with low common mode disturbance.

Figure 4:
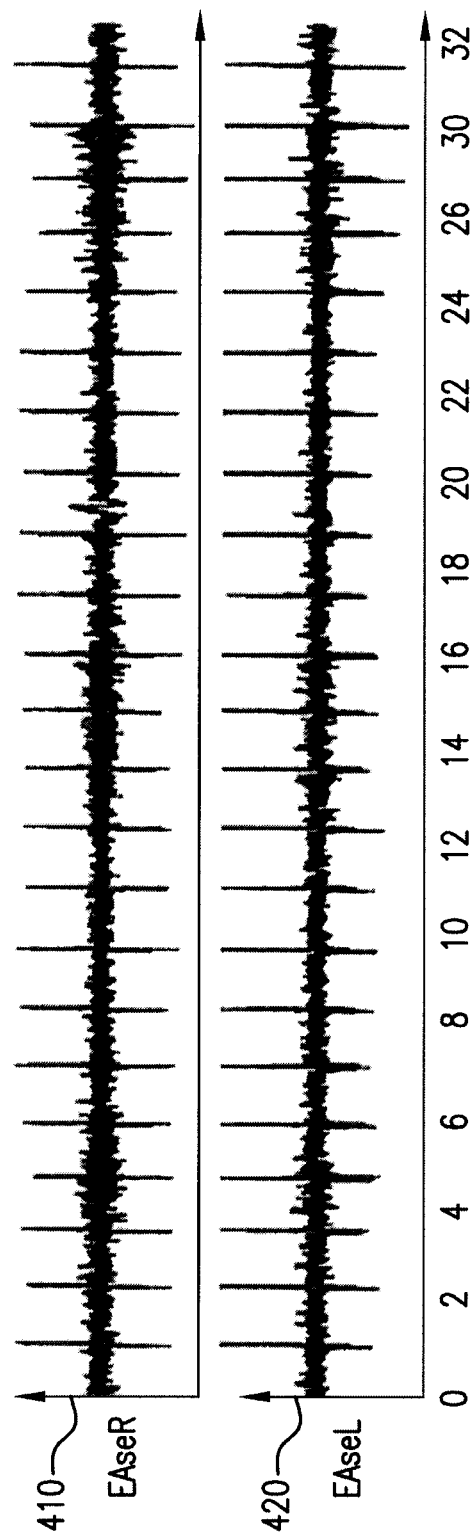
FIG. 4 is a pair of graphs showing electrical activity tracings obtained from surface electrodes positioned on left and right sides of the lower rib-cage of a patient.

FIG. 4 is a pair of graphs showing electrical activity tracings obtained from surface electrodes or electrode sets positioned on left and right sides of the lower rib-cage of a patient. A graph 410 shows a raw trace of an electrical activity signal obtained from a surface electrode placed on a right side of the patient's body (EAseR). A graph 420 shows a raw trace of an electrical activity signal obtained from a surface electrode placed on a left side of the patient's body (EAseR). A time axis, in seconds, is common to both graphs 410 and 420. As can be seen, the QRS complex of the electrical cardiac activity is synchronized between EAseL and EAseR.

Verification of EAse measurements is made in part by detection of electrical cardiac activity (a synchronized "compound" motor unit signal with amplitudes several-folds stronger than that of the interference pattern signal of respiratory muscles), where contralateral comparison of presence, frequency and interval of the waveforms, e.g. the QRS complexes states that both the system and the electrodes or electrode sets are properly functioning. This is based on the fact that cardiac signal strength can be measured despite obesity, paralysis or other factors limiting measurement of inspiratory muscle electrical activity.

Figure 5:
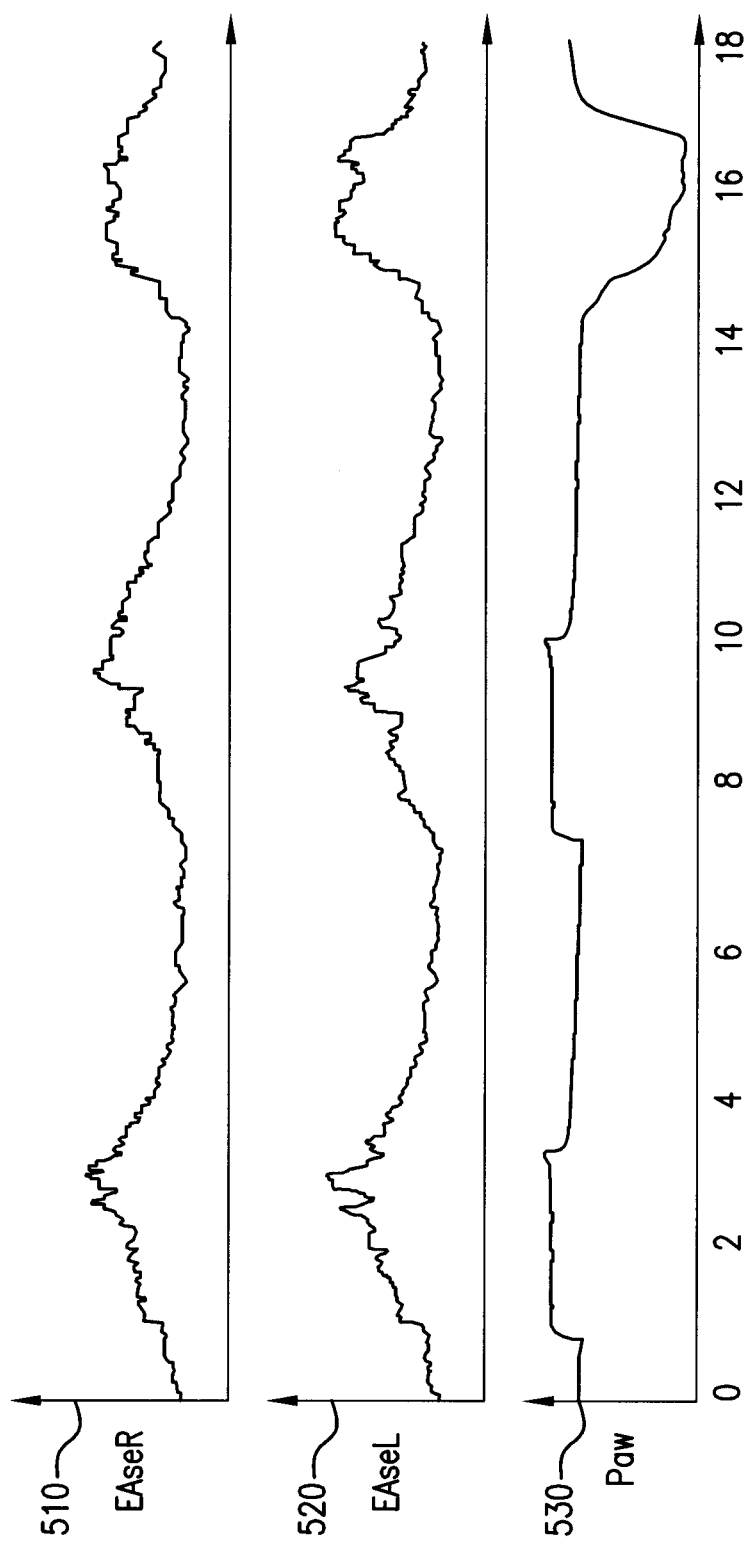
FIG. 5 is a pair of graphs showing tracings obtained by removing a cardiac signal from the electrical activity tracings of FIG. 4, with an additional graph showing an airway pressure signal obtained during assisted inspiration and during inspiration occlusion.

FIG. 5 is a pair of graphs showing tracings obtained by removing a cardiac signal from the electrical activity tracings of FIG. 4, with an additional graph showing an airway pressure signal obtained during assisted inspiration and during inspiration occlusion. A graph 510 shows the EAseR without the cardiac signal while a graph 520 shows the EAseL without the cardiac signal. A graph 530 shows a corresponding airway pressure (Paw) tracing. A common time axis, in seconds, applies to graphs 510, 520 and 530.

One non-limitative example of a statistical method that may be used to validate the inspiratory muscle activity of the patient includes a determination of phase differences between the EAseR and EAseL tracings of FIG. 5 to evaluate their synchrony. Another non-limitative example involves calculating integrals of their tracings over time, as a means to estimate the symmetry and proportionality of respiratory volumes on both sides. Yet another non-limitative example involves calculating mean values of these tracings over time segments, also to estimate the symmetry and proportionality of respiratory volumes. For example, these phase differences, integrals, and means values may be calculated in the comparator 260 to evaluate synchrony, symmetry and/or proportionality between the left and right electrical activity signals and compared to thresholds in the determiner 280 to validate inspiratory muscle activity.

Figure 6:
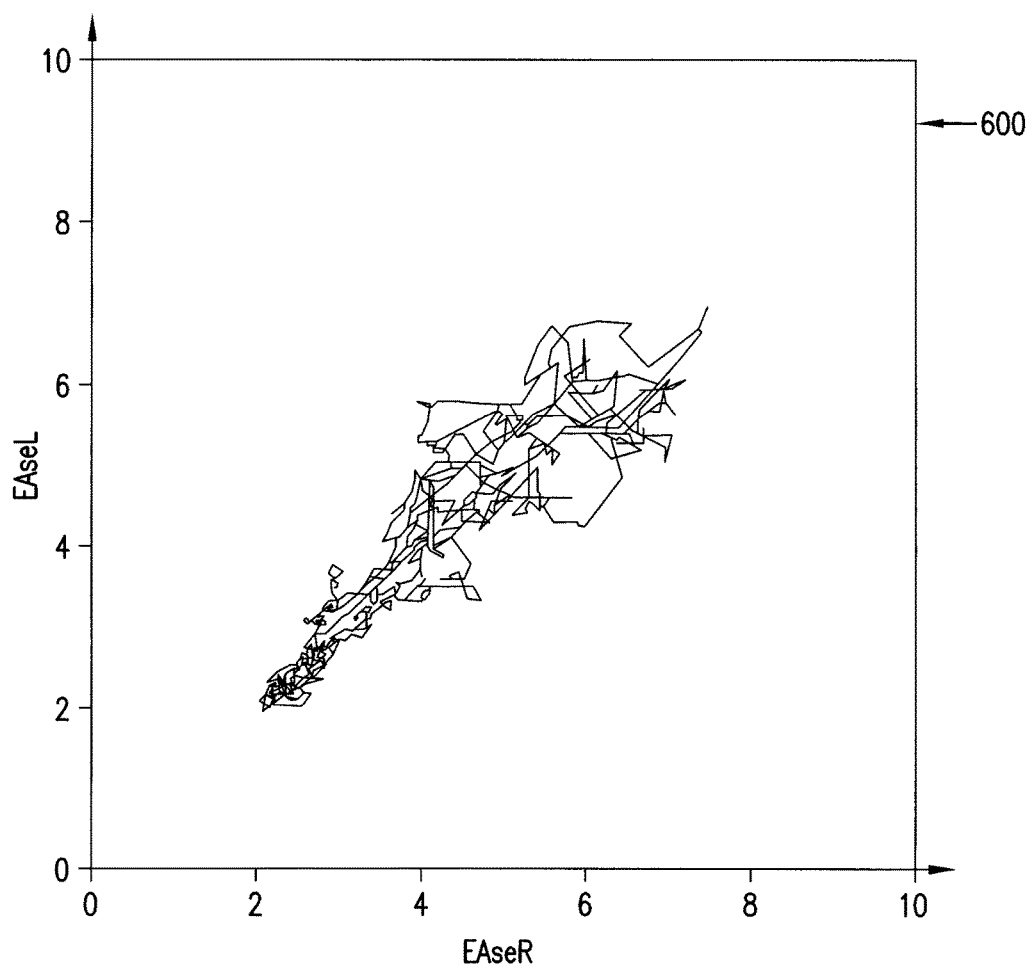
FIG. 6 is a graph showing a correlation between left and right, undisturbed electrical activity signals obtained during breathing.

FIG. 6 is a graph showing a correlation between left and right, undisturbed electrical activity signals obtained during breathing. A graph 600 shown in FIG. 6 is based on the same data as reflected on FIG. 5. Considering the graph 600, respiratory muscle activity in a patient who does not have neuro-muscular disorder/paralysis should occur with synchronized, symmetrical or proportional timing and amplitude. Thus, EAse occur bilaterally such that respiratory muscle activation displays generally synchronized, symmetrical or proportional signal pattern/waveforms between electrodes or electrode sets positioned bilaterally and symmetrically on the upper thorax or neck. Of course this would also apply to other respiratory related muscles as e.g. the alae nasi. This is based on the fact that the duration and magnitude of the inspiratory muscle activity waveform is similar/proportional bilaterally whereas other non-breathing related activity of the same muscles are not characterized by equal duration and magnitude of the inspiratory muscle activity waveform. Naturally, also the frequency content (frequency power spectrum analysis) of the EAse signal can be subjected to bilateral comparison.

As another example of an available statistical method, determination of sufficient synchrony, symmetry or proportionality to validate the inspiratory muscle activity of a patient may be obtained by calculating a correlation between successive values of EAseR and EAseL, using a correlation equation:

$$r = \frac{\sum_i (x_i - \bar{x})(y_i - \bar{y})}{\sqrt{\sum_i (x_i - \bar{x})^2} \sqrt{\sum_i (y_i - \bar{y})^2}}$$

wherein:
r is a correlation result;
i is an index of measurement points on each of EAseL tracings and EAseR tracings;
$x_i$ is a $i^{th}$ value of EAseL;
$y_i$ is a $i^{th}$ value of EAseR;
$\bar{x}$ is a mean value of EAseL; and
$\bar{y}$ is a mean value of EAserR.

The value of r is bound at a maximum of 1 for perfectly correlated tracings of EAseL and EAseR. In a practical application, the value of r is expected to vary based at least on the type of sensors used, on their position and on physiological characteristics of the patient. Again, the value of r may be calculated in the comparator 260 to evaluate synchrony, symmetry and/or proportionality between the left and right electrical activity signals and compared to thresholds (as non limitative example a threshold of 0.7) in the determiner 280 to validate inspiratory muscle activity. A correlation analysis of the data shown on the graph of FIG. 6 can provide additional insights to the caregiver, helping in the determination of the validity of the inspiratory muscle activity of the patient.

Figure 7:
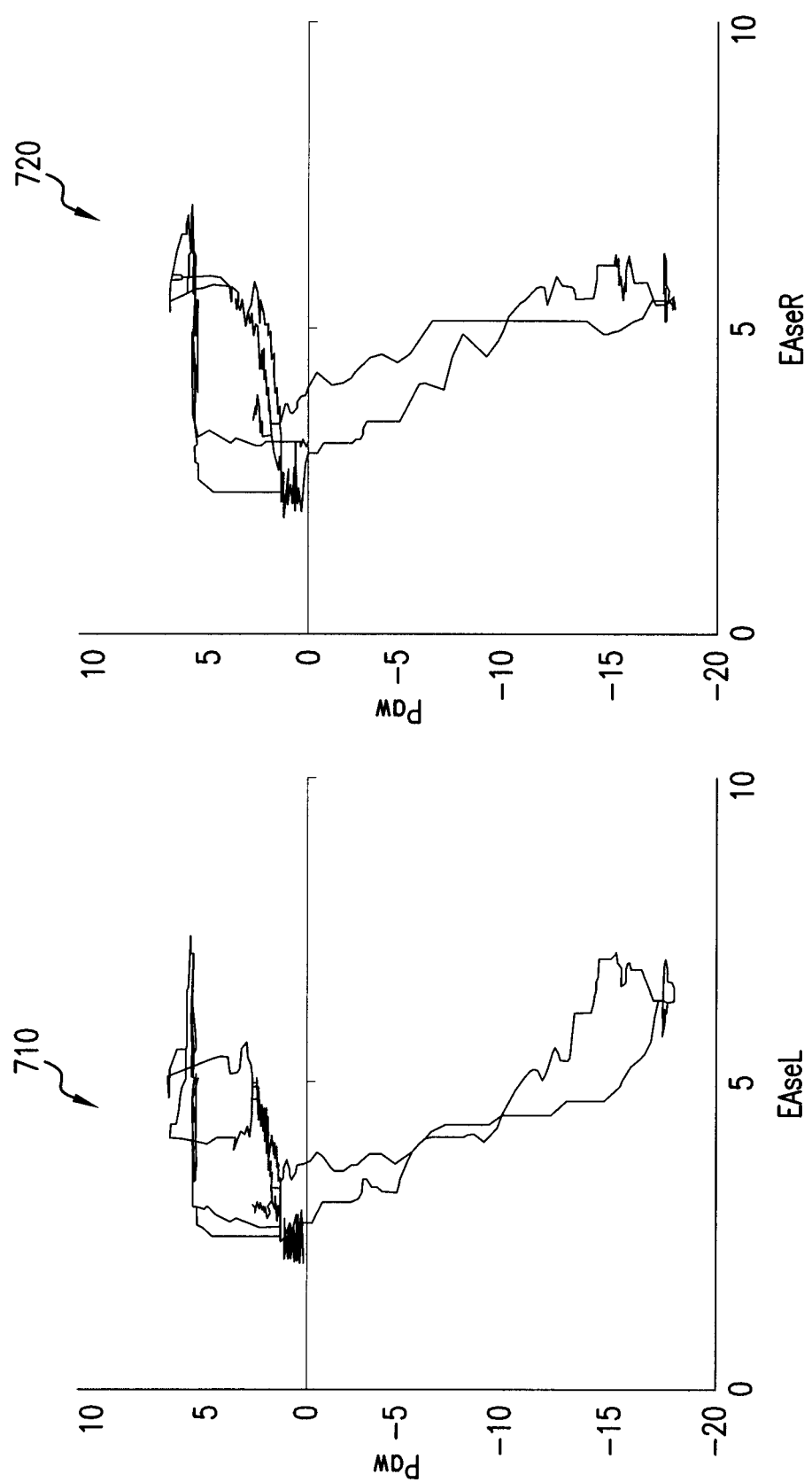
FIG. 7 is a pair of graphs showing a relation between airway pressure and left and right electrical activity during assisted inspiration and during inspiratory occlusion.

FIG. 7 is a pair of graphs showing a relation between airway pressure (Paw) and left and right electrical activity during assisted inspiration and during inspiratory occlusion. Graphs of FIG. 7 are based on the same data reflected on FIGS. 5 and 6. On graphs 710 (left electrical activity) and 720 (right electrical activity), positive airway pressure (Paw) values are obtained during assisted inspiration while negative Paw values are obtained during inspiratory occlusion. Airway pressure during an occluded inspiration (PinspOCCL) represents the cumulated mechanical effort of inspiratory muscle's and is in turn generated by cumulated neural inspiratory effort resulting in the inspiratory muscle electrical activity. As mentioned in the foregoing description of operation 180 of FIG. 1, inspiratory-EAse (EAseINSP) is expected be synchronized, proportional and inversely correlated with inspiratory occlusion pressure. This is based on the fact that inspiratory muscle activity and pressure are related. A correlation analysis of the data shown on the graphs of FIG. 7 can also provide insights to the caregiver, helping in the determination of the validity of the inspiratory muscle activity of the patient.

Figure 8:
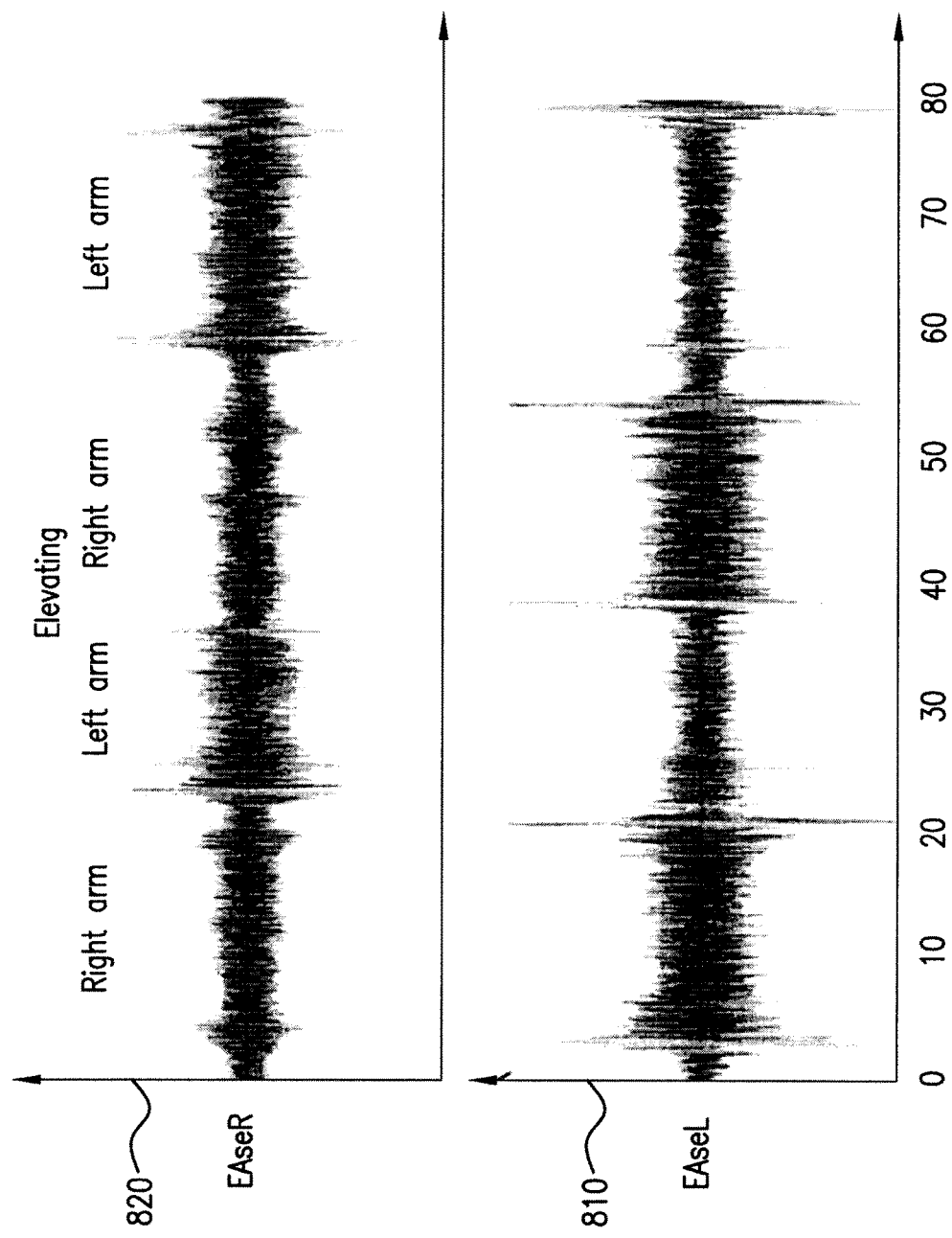
FIG. 8 is a pair of graphs showing electrical activity tracings similar to those of FIG. 4, the tracings including artifacts from muscles not participating in the inspiratory activity of the patient.

FIG. 8 is a pair of graphs showing electrical activity tracings similar to those of FIG. 4, the tracings including artifacts from muscles not participating in the inspiratory activity of the patient. A time axis in seconds applies to both tracings. In these tracings, the patient raised his right and left arms one after the other, causing significant artifacts within the electrical activity tracings in the form of clear temporo-spatial side-difference/asymmetry between EAseL 810 and EAseR 820. Postural activity is not expected to show a symmetrical and phasic waveform, but rather be arhythmical and show clear side differences. As a result, these artifacts can be filtered out from the tracings.

Figure 9:
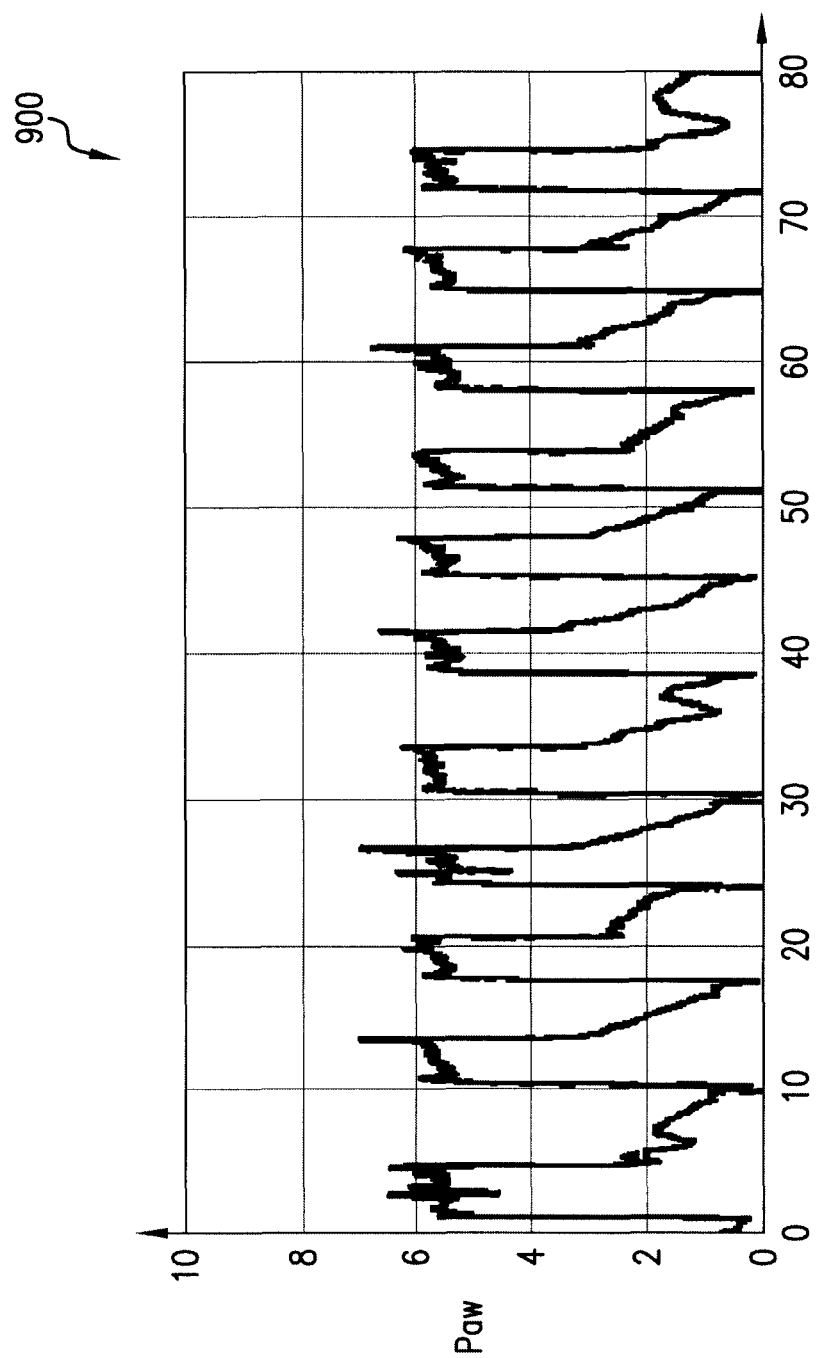
FIG. 9 is a graph showing an actual airway pressure measurement obtained using the method of FIG. 1.

FIG. 9 is a graph showing an actual airway pressure measurement obtained using the method of FIG. 1. Paw measurements are shown on graph 900 and relate to the electrical activity tracings of FIG. 8. A time axis is in seconds.

As indicated hereinabove, EAse signal segments fulfilling criteria to represent inspiratory muscle activity can be used for further analysis of e.g. patient-ventilator interaction, respiratory drive, spectral analysis for fatigue, and the like. For example, consistent unilateral correlation between unilateral EAse and PinspOCCL can suggest hemidiaphragm paralysis, for example following cardiac surgery. No EAse on either side in the presence of PinspOCCL can result from diaphragm paralysis and severe obesity. No EAse on either side and without PinspOCCL can result from apnea. Analyzing the above information one can conclude that: a breath where 1) contralateral EAse signal is synchronized in the left and right waveforms and 2) mean/sum/integral of EAse from each side is corresponding to changes in PinspOCCL has very high probability of representing EAse related to inspiratory muscles (EAseINSP).

Returning to FIG. 3, in an embodiment, the validating system 200 provides to the computer 350 the data related to the inspiratory signals, for the operator's or caregiver's benefit. The computer 350 presents the data on the monitor 360, for example in the form of the graph 600 as illustrated, or in the form of the various graphs illustrated in FIGS. 2-9.

Those of ordinary skill in the art will realize that the description of the method and system for validating inspiratory muscle activity of a patient and of the mechanical ventilation system are illustrative only and are not intended to be in any way limiting. Other embodiments will readily suggest themselves to such persons with ordinary skill in the art having the benefit of the present disclosure. Furthermore, the disclosed method and systems may be customized to offer valuable solutions to existing needs and problems of obtaining validated information related to inspiratory effort of a patient when avoiding use of invasive sensors.

In the interest of clarity, not all of the routine features of the implementations of the method and systems are shown and described. It will, of course, be appreciated that in the development of any such actual implementation of the method and systems, numerous implementation-specific decisions may need to be made in order to achieve the developer's specific goals, such as compliance with application-, system-, and business-related constraints, and that these specific goals will vary from one implementation to another and from one developer to another. Moreover, it will be appreciated that a development effort might be complex and time-consuming, but would nevertheless be a routine undertaking of engineering for those of ordinary skill in the field of mechanical ventilation systems having the benefit of the present disclosure.

In accordance with the present disclosure, the components, process operations, and/or data structures described herein may be implemented using various types of operating systems, computing platforms, network devices, computer programs, and/or general purpose machines. In addition, those of ordinary skill in the art will recognize that devices of a less general purpose nature, such as hardwired devices, field programmable gate arrays (FPGAs), application specific integrated circuits (ASICs), or the like, may also be used. Where a method comprising a series of operations is implemented by a computer or a machine and those operations may be stored as a series of instructions readable by the machine, they may be stored on a tangible medium.

Systems and modules described herein may comprise software, firmware, hardware, or any combination(s) of software, firmware, or hardware suitable for the purposes described herein. Software and other modules may reside on servers, workstations, personal computers, computerized tablets, personal digital assistants (PDA), and other devices suitable for the purposes described herein. Software and other modules may be accessible via local memory, via a network, via a browser or other application or via other means suitable for the purposes described herein. Data structures described herein may comprise computer files, variables, programming arrays, programming structures, or any electronic information storage schemes or methods, or any combinations thereof, suitable for the purposes described herein.

Although the present disclosure has been described hereinabove by way of non-restrictive, illustrative embodiments thereof, these embodiments may be modified at will within the scope of the appended claims without departing from the spirit and nature of the present disclosure.

What is claimed is:

1. A method of validating measurements of an inspiratory muscle activity of a patient, comprising:
   measuring the inspiratory muscle activity of the patient by acquiring from non-invasive sensors left and right electrical activity signals respectively representing activity of a left muscle and of a right muscle synchronized with an inspiratory effort of the patient;
   extracting a cardiac activity signal from the left and right electrical activity signals;
   determining whether the measurements of the inspiratory muscle activity of the patient are valid based on at least one of a synchrony, a symmetry or a proportionality of the left and right electrical activity signals from which the cardiac activity signal is extracted; and
   controlling a mechanical ventilator providing ventilatory assist to the patient via a breathing tube based at least in part on a determination that the measurements of the inspiratory muscle activity of the patient are valid.

2. The method of claim 1, wherein the non-invasive sensors are surface electrodes.

3. The method of claim 1, wherein the non-invasive sensors include a pair of electrode sets, each set including a plurality of electrodes.

4. The method of claim 1, comprising applying the non-invasive sensors bilaterally on the thorax, neck or nostrils of the patient.

5. The method of claim 1, wherein the left and right muscles synchronized with the inspiratory effort of the patient are located in the thorax, neck or nostrils of the patient.

6. The method of claim 1, wherein the non-invasive sensors are symmetrically placed on the patient's body.

7. The method of claim 1, comprising:
   correlating the left and right electrical activity signals from which the cardiac activity signal is extracted, the left and right electrical activity signals being acquired while an airway of the patient is occluded;
   wherein the measurements of the inspiratory muscle activity of the patient are determined to be valid when the left and right electrical activity signals from which the cardiac activity signal is extracted are proportional to an occluded inspiratory pressure of the patient.

8. The method of claim 1, comprising amplifying the left and right electrical activity signals before extracting the cardiac activity signal.

9. The method of claim 1, comprising processing the left and right electrical activity signals by applying an element selected from the group consisting of filtering, integrating, rectifying, averaging and a combination thereof to the left and right electrical activity signals.

10. The method of claim 1, comprising extracting from the left and right electrical activity signals artifacts caused by muscles not synchronized with the inspiratory effort of the patient.

11. The method of claim 1, comprising verifying at least one of a timing synchrony, a timing symmetry, a timing proportionality, an amplitude synchrony, an amplitude symmetry or an amplitude proportionality of the left and right electrical activity signals from which the cardiac activity signal is extracted.

12. A system for validating measurements of an inspiratory muscle activity of a patient, comprising:
- non-invasive sensors configured to measure the inspiratory muscle activity of the patient by acquiring left and right electrical activity signals respectively representing activity of a left muscle and of a right muscle synchronized with an inspiratory effort of the patient;
- an extractor of a cardiac activity signal from the left and right electrical activity signals;
- a first comparator configured to verify at least one of a synchrony, a symmetry or a proportionality of the left and right electrical activity signals from which the cardiac activity signal is extracted;
- a determiner responsive to the verification made by the first comparator to determine whether the measurements of the inspiratory muscle activity of the patient are valid;
- a mechanical ventilator;
- a breathing tube providing ventilatory assist from the mechanical ventilator to the patient; and
- a controller controlling the mechanical ventilator based at least in part on a determination that the measurements of the inspiratory muscle activity of the patient are valid.

13. The validating system of claim 12, wherein the non-invasive sensors are surface electrodes.

14. The validating system of claim 12, wherein the non-invasive sensors include a pair of electrode sets, each set including a plurality of electrodes.

15. The validating system of claim 12, wherein the non-invasive sensors are configured for bilateral application on the thorax, neck or nostrils of the patient.

16. The validating system of claim 12, wherein the non-invasive sensors are configured for symmetrical application on the patient's body.

17. The validating system of claim 12, comprising:
- a second comparator of the left and right electrical activity signals from which the cardiac activity signal is extracted, the left and right electrical activity signals being acquired while an airway of the patient is occluded;
- wherein the determiner is configured to determine that the measurements of the inspiratory muscle activity of the patient are valid when the left and right electrical activity signals from which the cardiac activity signal is extracted are proportional to an occluded inspiratory pressure of the patient.

18. The validating system of claim 17, comprising:
- an inspiratory valve mounted on the breathing tube; and
- an airway pressure meter mounted on the breathing tube;
- wherein the controller is adapted for providing commands to the mechanical ventilator to operate the inspiratory valve and to allow measurement of the occluded inspiratory pressure of the patient by the airway pressure meter.

19. The validating system of claim 12, comprising amplifiers of the left and right electrical activity signals, the amplifiers amplifying the activity signals before extraction of the cardiac activity signal.

20. The validating system of claim 12, comprising one or more of a filter, an integrator, a rectifier and an averager of the left and right electrical activity signals.

21. The validating system of claim 12, comprising an extractor operative to remove from the left and right electrical activity signals artifacts caused by muscles not synchronized with the inspiratory effort of the patient.

22. The validating system of claim 12, comprising a verifier of at least one of a timing synchrony, a timing symmetry, a timing proportionality, an amplitude synchrony, an amplitude symmetry or an amplitude proportionality of the left and right electrical activity signals from which the cardiac activity signal is extracted.

23. The mechanical ventilation system of claim 12, wherein the controller comprises a computer and wherein the mechanical ventilation system further comprises:
- a monitor operably connected to the computer and receiving therefrom an alert originating from the extractor or from the first comparator.

* * * * *